US 6,524,484 B2

(12) United States Patent
Davis et al.

(10) Patent No.: US 6,524,484 B2
(45) Date of Patent: Feb. 25, 2003

(54) ACCESS VALVE DEVICES, THEIR USE IN SEPARATION APPARATUS, AND CORRESPONDING METHODS

(75) Inventors: John Davis, Hucclecote (GB); Martin John Hofmann, Stroud (GB)

(73) Assignee: Amersham Pharmacia Biotech AB (SE)

( * ) Notice: Subject to any disclaimer, the term of this patent is extended or adjusted under 35 U.S.C. 154(b) by 0 days.

(21) Appl. No.: 09/920,748

(22) Filed: Aug. 3, 2001

(65) Prior Publication Data

US 2002/0023881 A1 Feb. 28, 2002

Related U.S. Application Data

(62) Division of application No. 09/495,359, filed on Feb. 1, 2000, now Pat. No. 6,277,283, which is a division of application No. 09/157,585, filed on Sep. 21, 1998, now Pat. No. 6,090,279, which is a division of application No. 08/825,026, filed on Mar. 26, 1997, now Pat. No. 5,902,485, which is a continuation of application No. PCT/GB95/02338, filed on Oct. 3, 1995.

(30) Foreign Application Priority Data

Oct. 3, 1994 (GB) .............................................. 9419888

(51) Int. Cl.⁷ ............................................. B01D 15/08
(52) U.S. Cl. .................... 210/656; 210/659; 210/198.2; 210/281
(58) Field of Search ................................. 210/656, 659, 210/198.2, 281; 95/82; 96/101, 103

(56) References Cited

U.S. PATENT DOCUMENTS

| | | | |
|---|---|---|---|
| 691,975 A | 1/1902 | Schaaf | 137/246.13 |
| 3,707,233 A | 12/1972 | Lerner | 210/281 |
| 3,777,892 A | 12/1973 | Thijssen | 210/178 |

(List continued on next page.)

FOREIGN PATENT DOCUMENTS

| | | | |
|---|---|---|---|
| EP | 0 007 783 | 2/1980 | 210/656 |
| EP | 0 059857 A1 | 9/1982 | 73/863.86 |
| EP | 0 776 243 | 6/1997 | 210/656 |
| FR | A 2 379 005 | 8/1978 | 137/240 |
| GB | 2 258 415 A | 2/1993 | 210/198.2 |
| GB | 2 307 028 | 4/1996 | 210/656 |
| NL | C 167338 | 11/1981 | 137/240 |
| WO | WO 95/20427 | 8/1995 | 210/635 |
| WO | WO 96/10451 | 4/1996 | 210/198.2 |
| WO | WO 00/25883 | 5/2000 | 210/635 |
| WO | WO 01/85329 | 11/2001 | 210/635 |

OTHER PUBLICATIONS

EPO Decision rejecting the opposition in EP 0 776 243 dated Feb. 13, 2001.
UK Courts Judgment in HC 1999 No. 01326 between Amersham Pharmacia Biotech AB (Claimant) and (1) Amicon Limited, (2) Millipore (UK) Limited and (3) Millipore Corporation (Defendants)dated Oct. 26, 2000 (Par. 1–48).

(List continued on next page.)

Primary Examiner—Ernest G. Therkorn
(74) Attorney, Agent, or Firm—Smith, Gambrell & Russell, LLP

(57) ABSTRACT

An access valve suitable for controlling fluid flow into and out of a chromatography column has a central axially movable probe with a head acting as a spool valve in a barrel. Axial movement of the probe adjusts the valve between a fully open condition, in which bota first conduit extending through the probe and a second conduit defined around the probe are open to the column interior, a partly open condition in which a second sealing land on the probe closes the second conduit, and a fully closed position in which both conduits are closed. The three positions are useful for packing and unpacking chromatography media into and from the column. In the closed condition of the valve, the first and second conduits communicate with one another so that the valve interior can be cleaned while the column is operating.

12 Claims, 10 Drawing Sheets

U.S. PATENT DOCUMENTS

| | | | |
|---|---|---|---|
| 3,874,825 A | 4/1975 | Jentsch | 417/517 |
| 4,178,249 A | 12/1979 | Councill | 210/281 |
| 4,224,108 A | 9/1980 | Takahashi et al. | 196/122 |
| 4,245,760 A | 1/1981 | Stevenson | 222/148 |
| 4,344,453 A | 8/1982 | Tuchenhagen et al. | 137/240 |
| 4,436,106 A | 3/1984 | Tuchenhagen et al. | 137/240 |
| 4,458,543 A | 7/1984 | Mieth | 73/863.86 |
| 4,478,707 A | 10/1984 | Bischoff et al. | 208/157 |
| 4,497,711 A | 2/1985 | Shepherd | 210/656 |
| 4,597,866 A | 7/1986 | Couillard | 210/198.2 |
| 4,724,074 A | 2/1988 | Schaupp | 210/163 |
| 4,743,373 A | 5/1988 | Rai | 210/198.2 |
| 4,871,463 A | 10/1989 | Taylor et al. | 210/161 |
| 4,891,133 A | 1/1990 | Colvin | 210/198.2 |
| 4,894,152 A | 1/1990 | Colvin | 210/198.2 |
| 4,976,865 A | 12/1990 | Sanchez et al. | 210/635 |
| 5,021,162 A | 6/1991 | Sakamoto | 210/656 |
| 5,141,635 A | 8/1992 | Leplang | 210/198.2 |
| 5,213,683 A | 5/1993 | Mann | 210/198.2 |
| 5,282,973 A | 2/1994 | Mann | 210/656 |
| 5,671,928 A | 9/1997 | Lanyi et al. | 277/207 R |
| 5,714,074 A | 2/1998 | Karlsson et al. | 210/656 |
| 5,902,485 A | 5/1999 | Davis et al. | 210/656 |
| 6,090,279 A * | 7/2000 | Davis | 210/198.2 |
| 6,277,283 B1 * | 8/2001 | Davis | 210/656 |

OTHER PUBLICATIONS

Millipore, "Automated Packing and Unpacking BioChromatography Process Columns", Publication No. BC1N007, date not provided but not considered prior art.

Amicon, "Automated Packing and Unpacking Biochromatography Process Columns", date not provided but not considered prior art.

Inventor sketch of device operating in Italy and supplied by Amicon (UK) (Undated).

Mann Welding Co. "Chromaflow" brochure, date not provided on document (4 pages).

\* cited by examiner

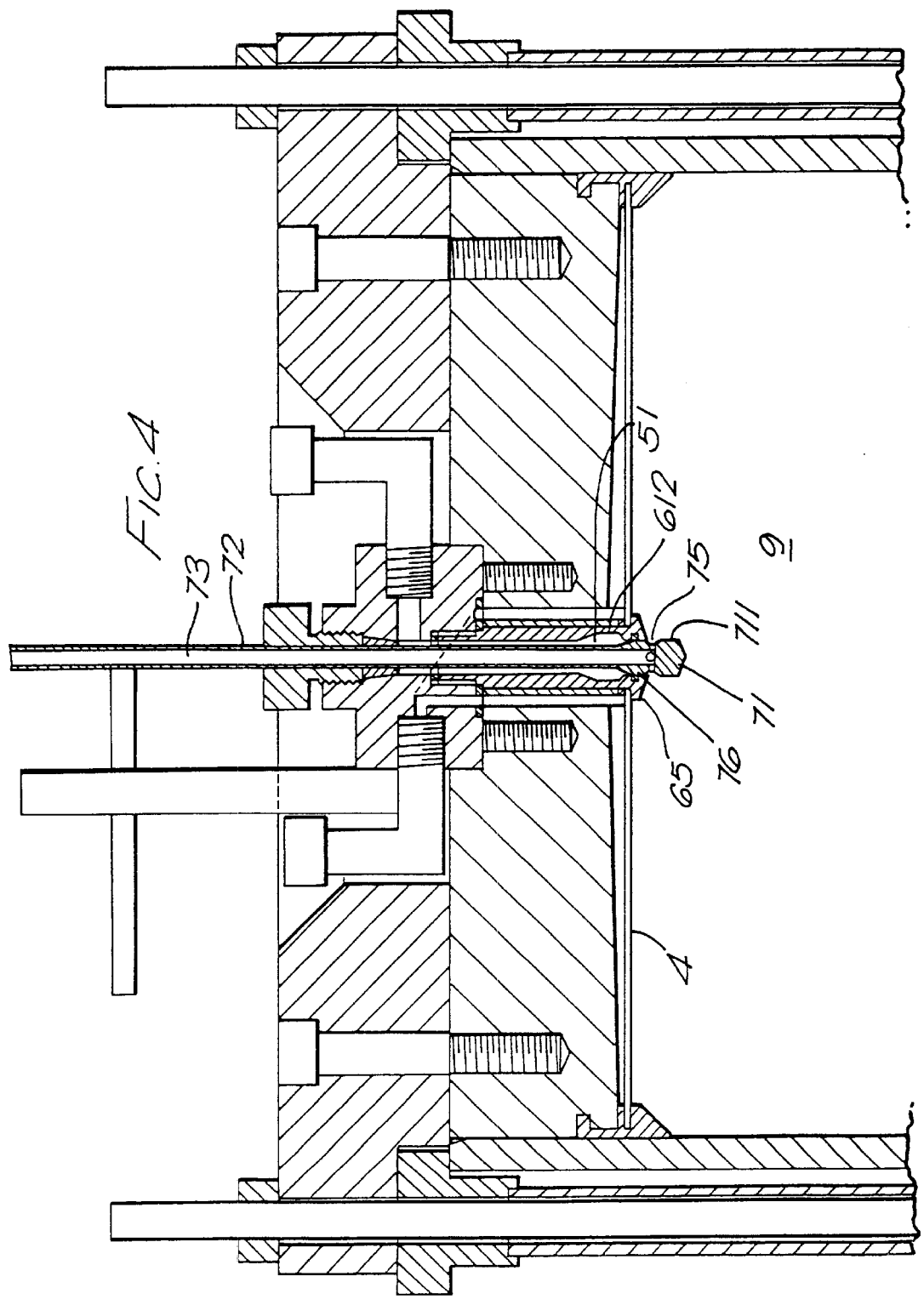

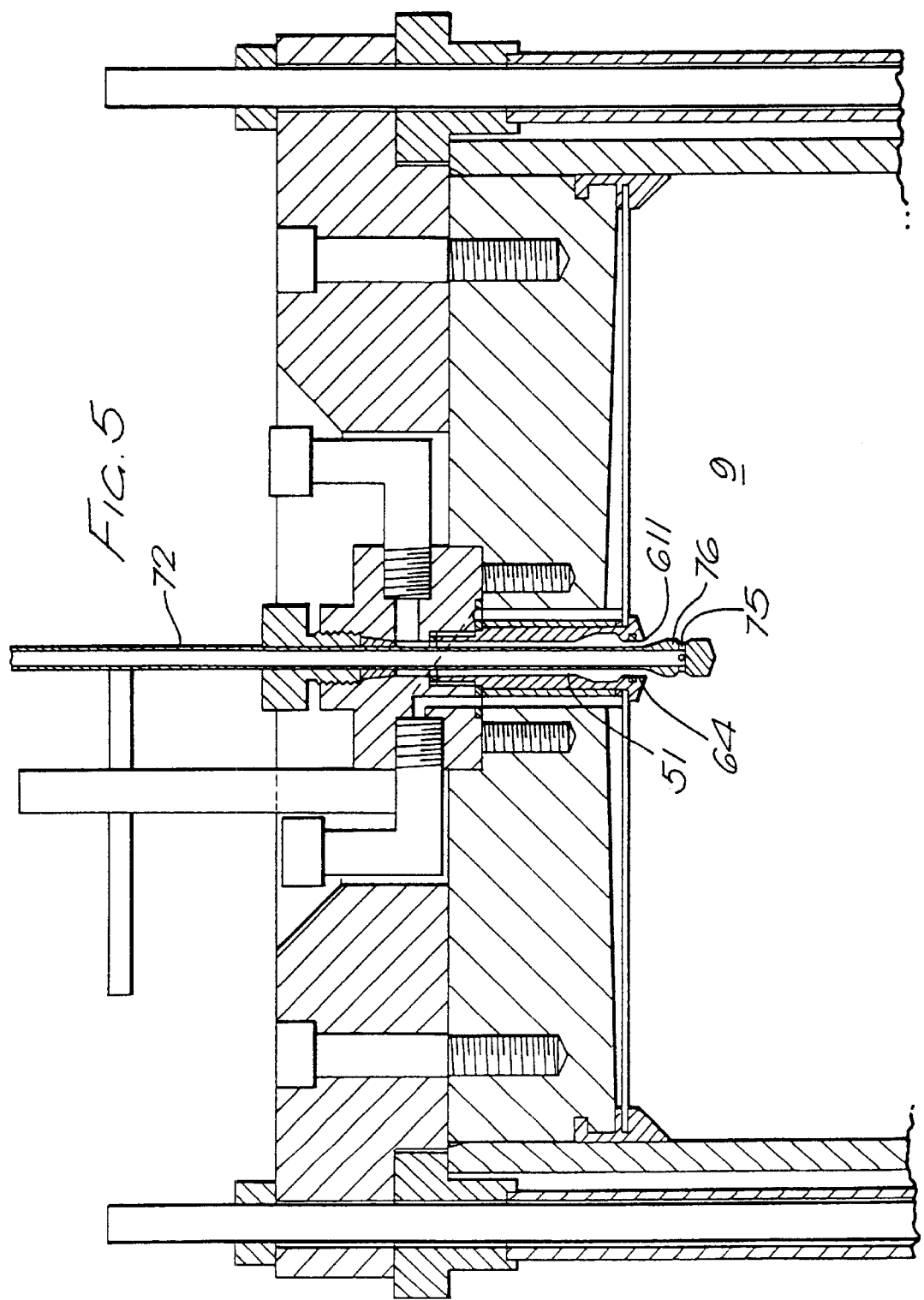

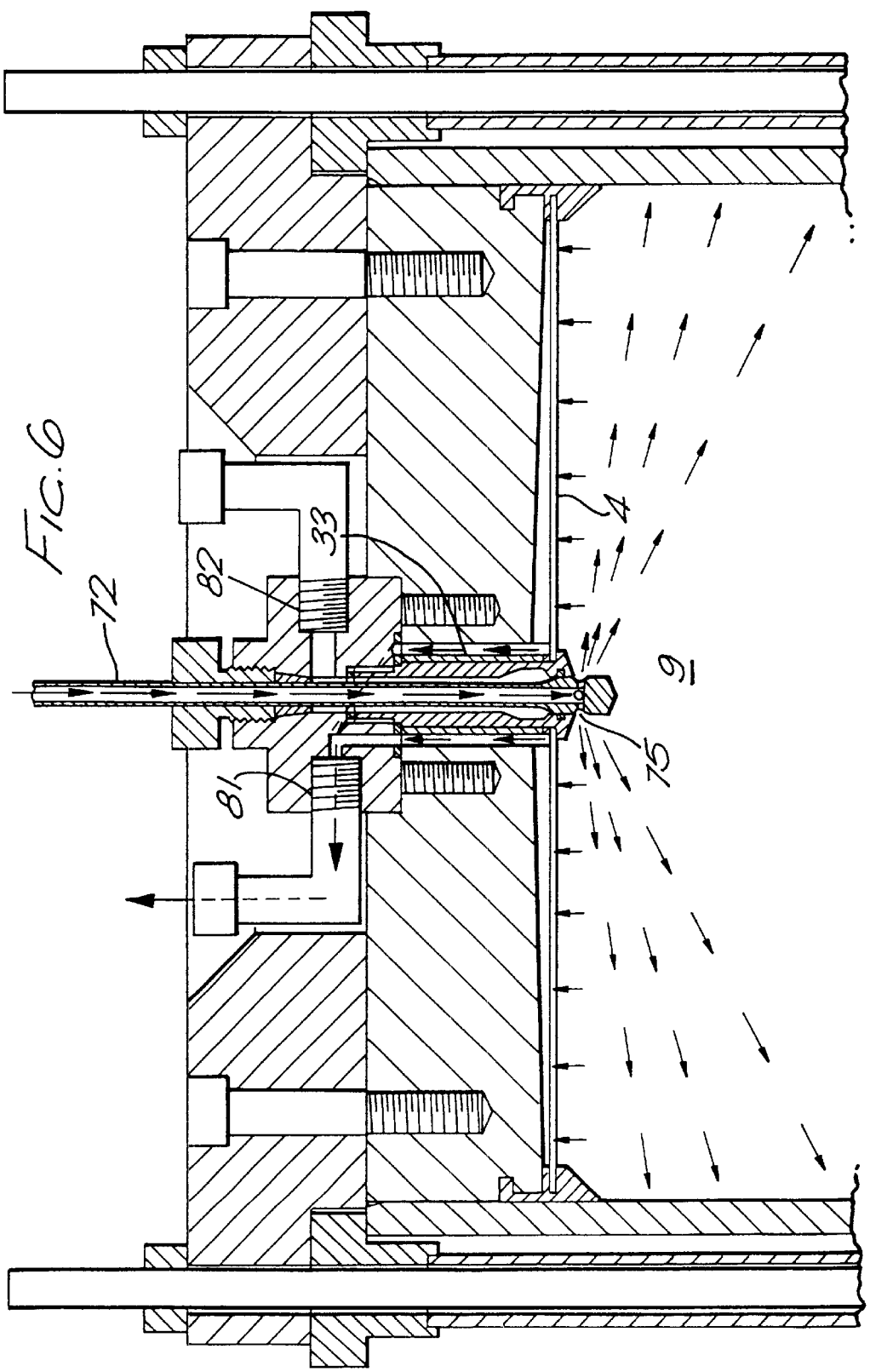

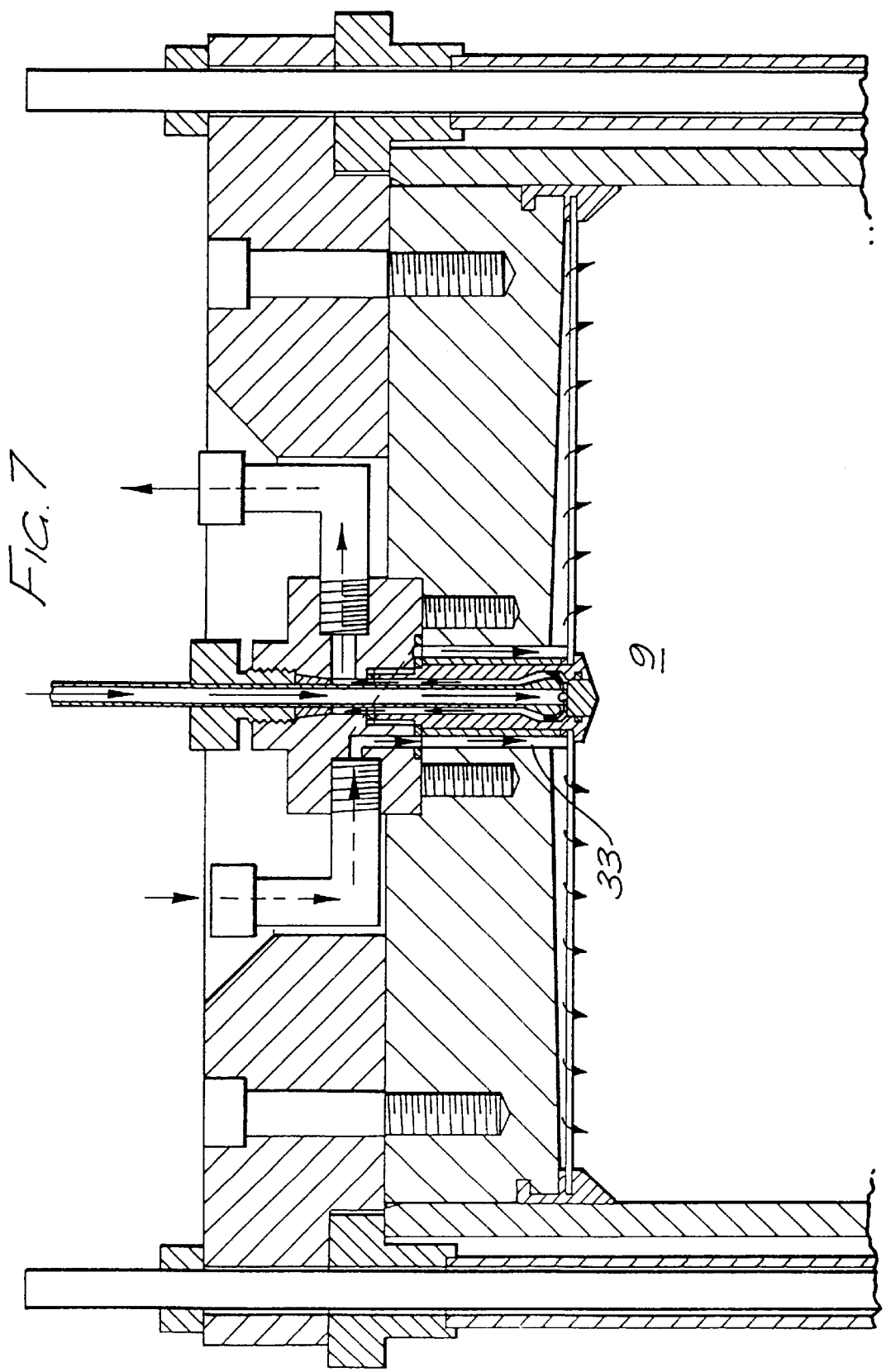

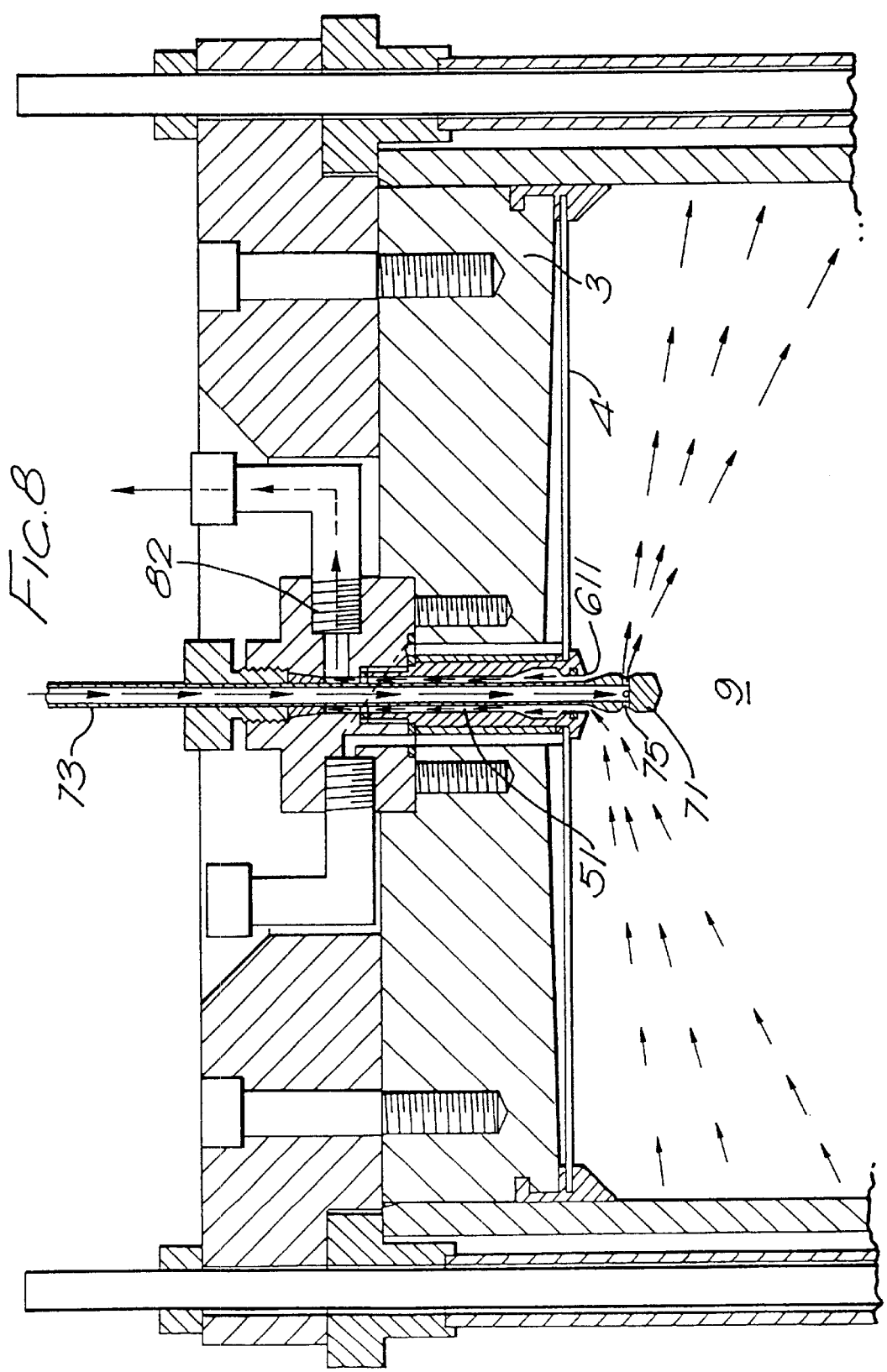

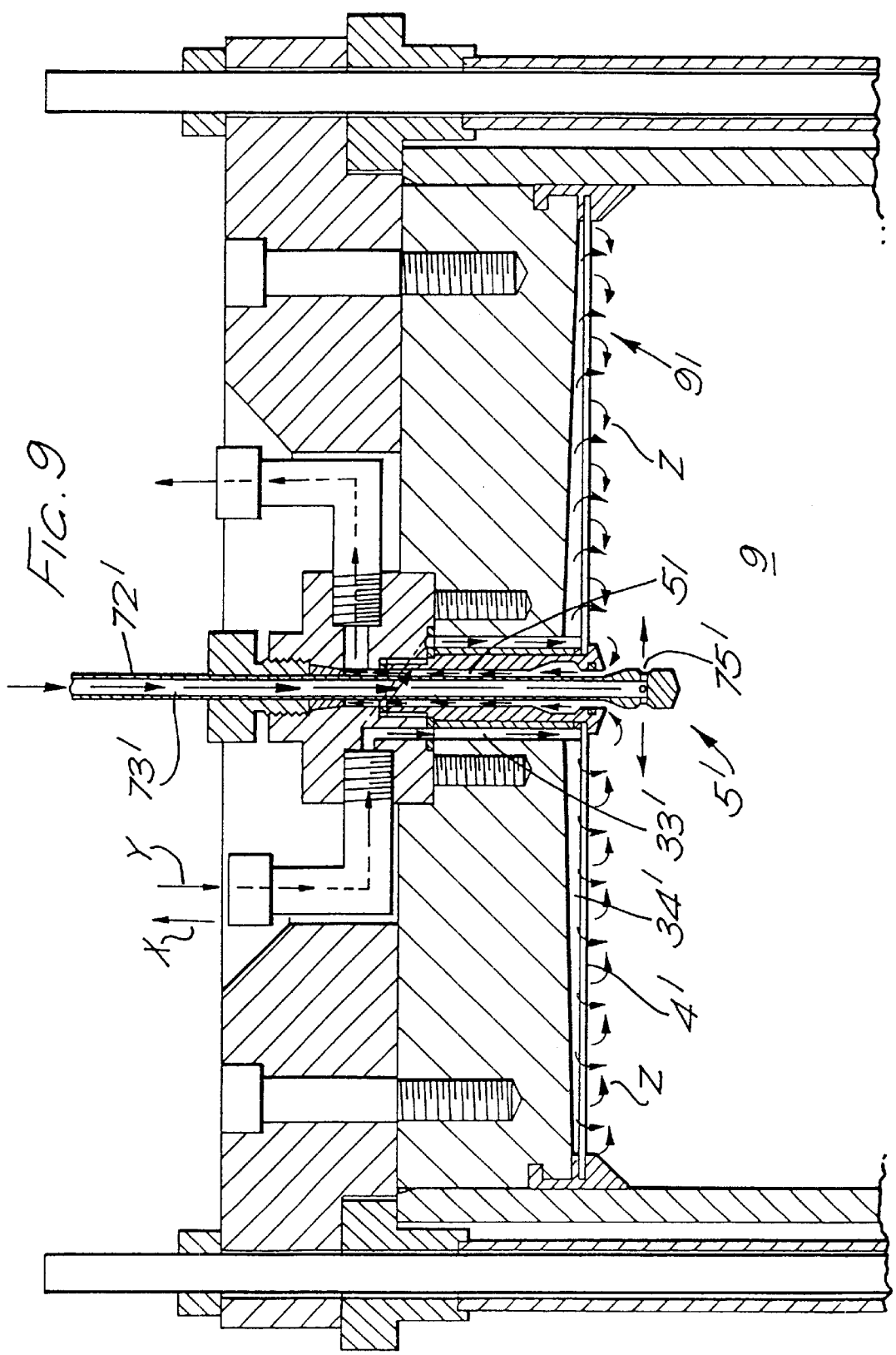

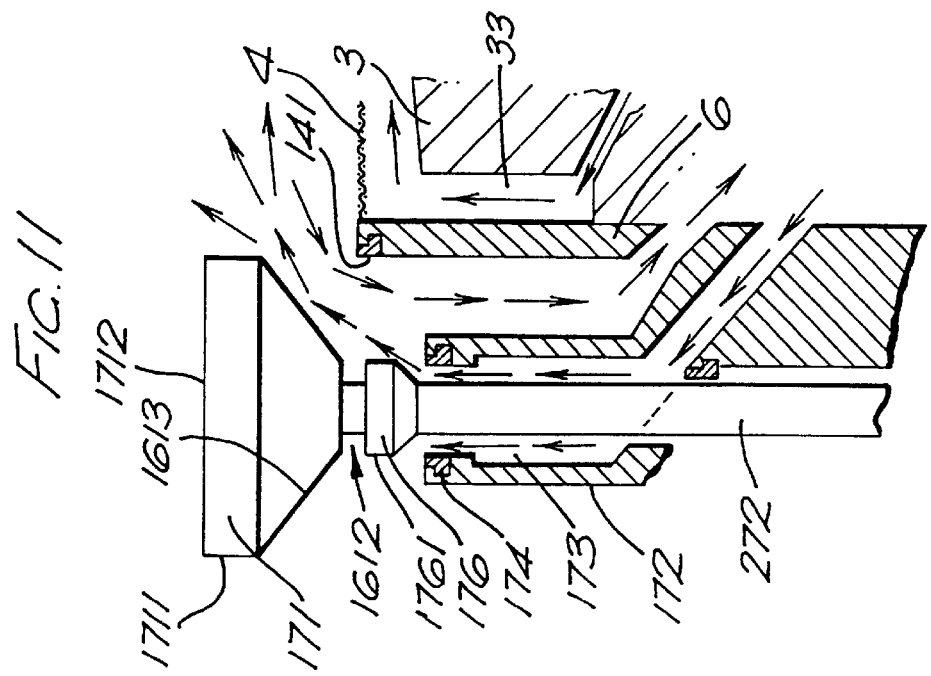
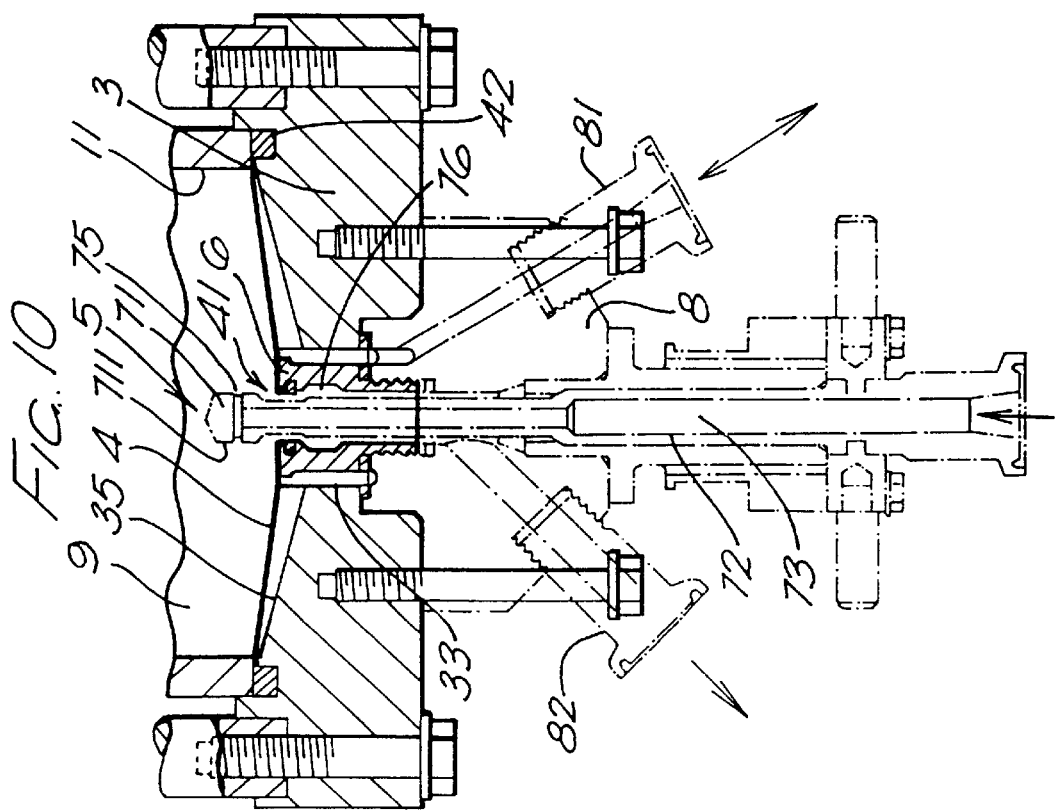

ACCESS VALVE DEVICES, THEIR USE IN SEPARATION APPARATUS, AND CORRESPONDING METHODS

This application is a Divisional of U.S. patent application Ser. No. 09/495,359 filed on Feb. 1, 2000, now U.S. Pat. No. 6,277,283 which is a Divisional of U.S. patent application Ser. No. 09/157,585, filed Sep. 21,1998, now U.S. Pat. No. 6,090,279, which is a Divisional of U.S. patent application Ser. No. 08/825,026, filed Mar. 26, 1997, now U.S. Pat. No. 5,902,485, which is a continuation of PCT/GB95/02338 having an international filing date of Oct. 3, 1995. PCT Patent Application No. PCT/GB95/02338 is incorporated herein by reference.

FIELD OF THE INVENTION

This specification relates to methods and apparatus for the control of fluid flow, e.g in chromatography, i.e. apparatus and methods for separating substances by passing a mobile phase through a stationary or retained phase to cause separation of mobile phase components.

BACKGROUND

Chromatography is a well-established and valuable technique in both preparative and analytical work as well as in purification generally. Typical industrial chromatography apparatus has an upright housing in which a bed of packing material, usually particulate, rests against a permeable retaining layer. Fluid mobile phase enters through an inlet e.g at the top of the column, usually through a porous, perforated, mesh or other restricted-permeability layer, moves through the packing bed and is taken out at an outlet, typically below a restricted-permeability layer.

Changing the bed of packing material, because it is spent or in order to run a different process, is an arduous task particularly with big industrial columns which can be hundreds of liters in volume. The existing bed has usually become compacted and difficult to remove. The housing must be dismantled, the compacted packing mass disrupted and then removed. Furthermore, the new bed must be very evenly packed if the column is to be effective: the fresh material must be added carefully while maintaining a flow of liquid. Usually the apparatus must be kept clean, particularly with biological products where high system sterility may be needed for weeks or even months. One small contamination can be disastrous.

Conventionally, many hours have been needed to change the spent packing in a big column.

GB-A-2258415 describes a column which can be packed and unpacked without taking it apart, using special supply and discharge valves in the top and bottom plates of the housing. The packing supply valve has a spray nozzle which can be retracted into the top plate, with the spray openings closed by a seal on the plate, or advanced to project into the column bed space, freeing the openings for a slurry of packing material to be pumped in. The discharge valve has an advanceable nozzle with radially-directed spray openings at its enlarged head, positioned coaxially within a wider bore of the bottom plate. When retracted, the head fits in the bore to seal itself and the bore. To empty the column, the nozzle is advanced and buffer liquid pumped through it. The advanced nozzle head breaks up the packed medium and the pumped-in buffer carries it out through the larger bore, now opened.

There are difficulties in maintaining long-term sanitary conditions with these valve assemblies.

THE INVENTION

We now propose further developments.

In one aspect we provide separation apparatus having a column housing whose housing wall defines an enclosed bed space which in use contains a bed of packing material. The housing wall includes end walls at opposite ends (in terms of an operational fluid flow direction) of the bed space and having inlet and outlet openings for fluid communication to and from the bed space in use. An access valve device communicates with the bed space through the housing wall at an access location. This valve device has first and second adjacent fluid-flow conduits, each having an exterior connection and an interior opening adjacent the housing wall interior. The valve device is controllably adjustable, from outside the housing wall, between a first, closed condition in which the first and second conduits are both isolated from the bed space;

a second, partially-open condition in which the device puts the first conduit in communication with the bed space but isolates the second conduit from the bed space, and a third, open condition in which the device puts the first and second conduits both in communication with the bed space.

An access valve of this type offers a number of possible operational advantages. Some are described later. One feature it can offer is packing and unpacking a bed space through a single housing wall installation. The relevant processes may be as follows.

To unpack, the valve is moved to the third condition in which both the first and second conduits are open to the bed space. Fluid is forced in through the first conduit to disrupt and disperse the packed bed, the flowable dispersion of the packing material then flowing out through the second conduit.

Preferred features for these purposes include the following.

The opening of the first conduit may have a spray nozzle or other restriction, fixed or adjustable, to help disrupt the bed by flow velocity. Having plural outlet openings also helps to reach a larger region of the bed space and clear it more effectively.

The access valve device preferably comprises a probe which, from a retracted condition recessed into the housing wall, can be advanced into the bed space to disrupt material therein. The disrupting probe is preferably a movable valve element defining one or both of the conduits, preferably the first conduit at its outlet (which may be at or through the head of the probe e.g. as in GB-A-2258415).

The opening of the second conduit may form an outlet from the bed space. Desirably it is a single aperture. Desirably it has cross-sectional area at least a substantial proportion of the cross-sectional flow area within the second conduit itself. Desirably the cross-sectional area of the second conduit through the valve device is generally larger than that of the first conduit.

To pack, the access valve device can be adjusted to the second, partially-open condition and packing material forced in through the first conduit, typically as a dispersion of particles in carrier fluid. Carrier fluid escapes from the bed space through an outlet remote from the valve device, while packing material is retained.

Thus, a bed of new packing material can be packed against a permeable end retainer at a housing wall location spaced from and preferably opposed to that of the valve device, by maintaining a flow of carrier fluid through the accumulating bed and out through the end retainer. This flow of carrier fluid can accompany the injection of bed material through the first conduit.

The valve device preferably has relatively movable valve parts or elements which are movable in or into face-to-face sealing contact with one another, and defining the first and second conduits. A pair of such elements may be sufficient to define the first and second conduits and also sealing portions or lands sufficient for shutting off their inward openings for the three conditions mentioned above. Respective spaced sealing portions on one part or element can sealingly engage a single sealing portion, or plural differently-spaced sealing portions, on the other relatively movable part or element to provide the first and second conditions.

The relative movement between the valve elements passing between the three conditions may be linear (typically in the direction through the housing wall, preferably perpendicularly), rotational (typically around a direction axis as specified above) or a combination of these e.g. moved linearly by a screw thread action. The three conditions desirably correspond to three spaced stations along a predetermined single rotational, linear or combination (e.g. helical) path or track for such relative movement.

For simplicity one such valve element may have a single sealing land which in the closed condition isolates the first conduit from the bed space and in the partially-open condition isolates the second conduit from the bed space. This land may be on a said valve element fixed relative to the housing wall, provided at or adjacent a mouth of the valve device. The openings of the first and second conduits can then be defined by one or more further valve elements which is/are slidably moveable relative to that sealing land.

Valves as proposed above are also usable to govern flow into/out of any vessel or conduit; not only separation apparatus housings.

It is a particularly desirable feature for a component of a separator apparatus, and also in other contexts, that it be cleanable in place ("CIP") i.e. without removing it from the apparatus and most preferably without interfering with the bed space e.g. while separation is in progress.

In a further aspect we propose that this be achievable, in an access valve device governing the communication of first and second conduits through the housing wall of a separator apparatus bed space as described, or through the well of any vessel or conduit into a space, by arranging that in a closed condition of the valve in which both first and second conduits are isolated from the space a continuous cleaning path is defined along the first conduit, through e.g. a cleaning recess in the valve device connecting between the first and second conduits, and along the second conduit. The valve device components are shaped such that, for cleaning fluid flow in at least one direction along the cleaning path, all regions thereof are swept i.e. there are no dead spaces. In particular, for at least one said flow direction at no point in the valve device does the surface of the first conduit, second conduit or the connecting recess diverge from or converge towards the central flow axis (or layer, according to the flow path shape) at a right-angle or greater, and preferably not at an angle greater than 70°.

One particular proposal provides the possibility of such a flow path in a three-condition valve device as proposed above, having relatively movable valve elements, one of the elements having an isolating seal which seals in the first condition against a first opposed sealing surface of the other element and in the second condition seals against a second opposed sealing surface of the other element, isolating the first and second conduits respectively from the bed space. According to our proposal the one valve element defines a recess behind its isolating seal which, in the closed condition, provides clearance around the second sealing surface of the other element to put the first and second fluid conduits in communication with one another.

In separation apparatus, a preferred location for an access valve in any of the aspects described above is in an end wall construction of the housing. This end wall is typically fluid-permeable but impermeable to the relevant packing material, e.g. by virtue of a porous, perforated or mesh layer—a filter layer. The access valve openings open to the bed space side of this layer. Generally further openings are provided for introducing fluid material, e.g. a sample or mobile phase generally, behind that filter layer e.g. along a third conduit which extends through the end wall alongside the valve device.

Another aspect provides uses of an access valve device as described for removing material from a column bed space, and in an additional version this may be part of a separation process.

The additional version relates to a separation process in which a liquid incorporating components to be separated is caused to flow upwardly through a bed of particulate stationary phase (packing medium) enclosed in a bed space of a column housing, for example at a rate which expands or fluidises the bed. After passing through the bed the liquid passes a restricted-permeability element (typically a mesh, or a porous or other perforated layer which will retain the packing medium particles) and out of the column housing through a process outlet.

The liquid may incorporate particulate or cohesive matter which will not pass, or not freely pass, the restricted-permeability element. Biological culture products are an important example of this. For instance, expanded bed separation is used to remove a target protein, by adsorption onto the bed particles, from an unclarified or partially-clarified culture broth containing cells, cell debris, lipid particles and/or the like.

As separation proceeds, such materials accumulate against the restricted-permeability element used to prevent escape of packing material through the process outlet. In time, the accumulated matter prevents effective operation. Processing must be stopped, the column housing opened and the accumulated matter cleared before restarting.

Our proposal is to remove such accumulated matter from the bed space, e.g. from time to time as the process proceeds, and optionally without cutting off the input of feed stock liquid, by opening a clearing outlet for accumulated matter at a location at or adjacent the restricted-permeability element and communicating directly with the bed space, and forcing a clearing flow of fluid at, across and/or back through the restricted-permeability element to disturb the accumulated matter so that it passes out through the clearing outlet.

So, the separation process may continue with reduced or eliminated interruptions for clearance of accumulated matter from the bed space.

The clearing flow may be provided by forcing a reverse flow through the restricted-permeability element, e.g. back through the process outlet, or through other conduits penetrating the impermeable wall behind the restricted-permeability element. Additionally or alternatively the clearing flow may come through one or more nozzles on the bed space side of the element by pumping fluid out of them e.g.

at the centre of the element, and desirably with a clearing flow radiating from a conduit penetrating the housing wall.

These functions may be served by an access valve device as disclosed in the previous aspects above.

Another proposal in the context of such a process involves the introduction of a mobile phase into the column bed space through a direct input opening, preferably valve-governed, rather than through a restricted-permeability element which is provided to retain the inlet side of the packing bed. For example, introduction is through an access valve device opening through the restricted-permeability element.

In this way a mobile phase incorporating particulate matter, or other matter which might clog the restricted-permeability element, can be introduced conveniently into the bed for processing. The access valve device used for the introduction may be e.g. any as described above.

By combining this proposal with the previous one, the introduced particulate or other matter can then conveniently be cleared from the bed space.

A further aspect provided herein is a valve device for governing flow through a housing or conduit wall into a space, e.g for a chromatography column housing wall. The valve device has an outer barrel element defining an axial direction. The barrel has an internal bore extending axially from an outer end to an inner end of the barrel, with axially-directed openings at both ends. The opening at the inner end constitutes a valve mouth, and provides a radially-inwardly directed mouth sealing surface of the bore.

An elongate spool element extends axially through the barrel bore and is axially movable relative to it. A central fluid conduit extends axially through the spool element, and opens adjacent the barrel mouth preferably by plural radially-directed openings, preferably as a spray nozzle. The spool element has a first, inner radially-outwardly directed sealing land disposed axially inwardly of the central conduit opening and adapted to seal against the barrel's mouth sealing surface in a first relative longitudinal position of the spool element relative to the barrel, thereby isolating the central conduit opening from the valve mouth.

The spool element also has a second, outer radially-outwardly directed sealing land disposed axially outwardly of the central conduit opening and adapted to seal against the barrel's mouth sealing surface in a second, intermediate longitudinal position of the spool element relative to the barrel in which the central conduit opening is exposed to the interior space. Outwardly of the second sealing land is a spacing, preferably annular, between the spool element and the barrel bore. This spacing constitutes an outer axially-extending fluid conduit which in a second, intermediate position is isolated from the valve mouth by the sealing of the second land.

In a third, inward position of the spool element relative to the barrel the second sealing land is clear of the mouth sealing surface and both the inner and outer conduits are open to the interior.

This valve device is suitable for use in all of the above aspects.

The barrel bore may have a recess disposed outwardly of the mouth sealing surface and connecting the inner conduit opening to the outer conduit in the fully-closed position.

The valve may be installed in the wall with the valve mouth at the wall interior and at the wall exterior a connecting manifold providing a fixed communicating connection to the outer conduit at the outer end of the barrel and a movable communicating connection to the inner conduit of the spool element. Means for driving controllable movement of the spool element is also provided. This may take various forms which a skilled person can provide without difficulty. For example, as disclosed in GB-A-2258415 the spool element may be thread-mounted into the manifold or another fixed component, the drive means functioning to rotate it to a controlled extent to give the desired axial shift.

In separation apparatus the valve may be installed in an end wall having an inner restricted-permeability layer and an outer impermeable wall layer, the valve mouth communicating through the restricted-permeability layer. The outside of the barrel at the mouth may overlap the restricted-permeability layer to trap it. To introduce process fluids into the bed space, one or more process conduits lead through the impermeable wall layer to behind the restricted-permeability layer, e.g. alongside the valve barrel as one or more clearances between the valve barrel and the surrounding impermeable layer of the end wall.

BRIEF DESCRIPTION OF THE DRAWINGS

Embodiments of our proposal are now described in detail, with reference to the accompanying drawings in which

FIG. 4 is an axial cross-section corresponding to FIG. 2 with the access valve in a part-open position;

FIG. 5 is an axial cross-section corresponding to FIG. 2 but with the access valve in a fully-open position;

FIG. 6 is an axial cross-section of the end plate illustrating a medium packing operation;

FIG. 7 is a view corresponding to FIG. 6, with the column in operation and the access valve being cleaned;

FIG. 8 is an axial cross-section corresponding to FIG. 6 illustrating the process of unpacking a packing medium from the column;

FIG. 9 is an axial cross-section of the top end plate of a chromatography column undergoing expanded-bed chromatography, illustrating a clearing operation;

FIG. 10 is an axial cross-section of a column end which is a variant of that in FIGS. 2 to 8; and FIG. 11 is a schematic view of a second version of the access valve.

DETAILED DESCRIPTION OF EMBODIMENTS

Figure 1:
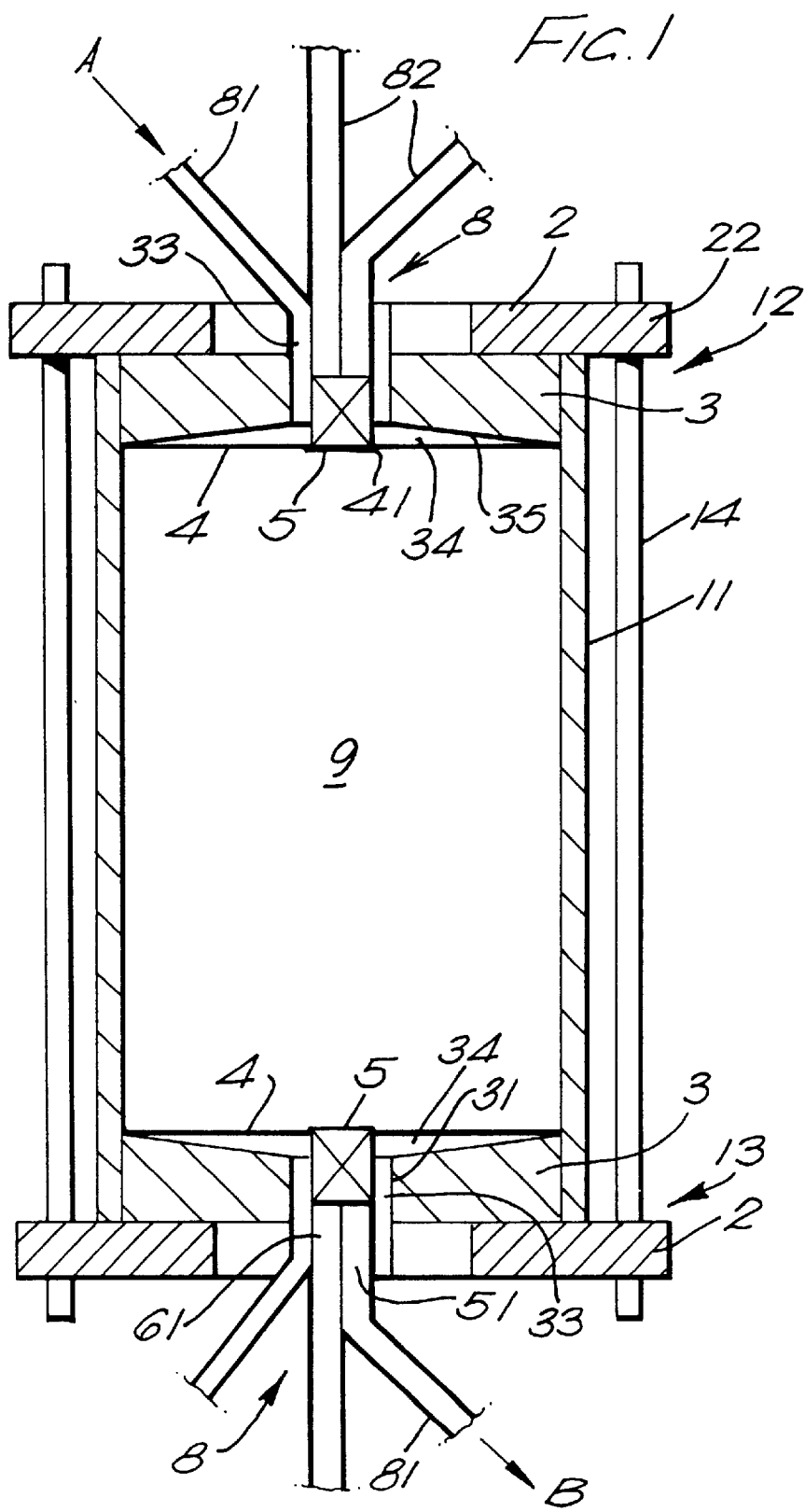
FIG. 1 is a cross-sectional schematic side view of a chromatography column showing the basic features thereof.

FIG. 1 shows schematically the general components of a chromatography column 1. The column has a cylindrical fluid-impermeable side wall 11, e.g. of stainless steel or a high-strength/reinforced polymeric material which may be translucent. The open top and bottom ends of the side wall 11 are closed by top and bottom end assemblies 12,13. Each end assembly has a fluid-impermeable end plate 3 fitting sealingly to plug the opening of the cylindrical wall 11, and preferably of stainless steel or high-strength engineering plastics material, e.g polypropylene. The end plates are backed up by metal retaining plates 2 bearing against their outer surfaces and projecting radially beyond the side wall as retaining flanges 22 through which adjustable tension rods 14 are secured. These link the top and end assemblies 12,13 and help the construction to withstand high fluid pressures.

Each end plate 3 has a central through-opening 31 for communication between the exterior of the column and the packing bed space 9 defined by the side wall 11 and end assemblies 12, 13. Access through the opening 31 is subdivided into separate conduits, connected externally through a connection manifold 8.

A filter layer 4, typically of filtered or woven plastics or steel, extends across the area of the bed space 9 at the inner surface of the end plate 3. The inner surface 35 of the end plate 3 is recessed behind the filter layer 4, e.g. conically as illustrated, and preferably with the use of support ribs (not indicated) supporting the filter layer 4 from behind, to define between them a filtration space 34. One of the communication conduits, a mobile phase conduit 33, opens inwardly into this filtration space 34, as well as outwardly to a mobile phase connector 81 of the manifold 8.

From the manifold 8, an access valve device 5 projects inwardly through the end plate opening 31 and sealingly through a central orifice 41 of the filter layer 4. The access valve 5, embodiments of which are described in more detail below, governs the communication of one or more conduits from the manifold 8 directly to the bed space 9, i.e. bypassing the filter layer 4. Indicated here are first and second valved conduits 51, 61 governed by the valve 5, and connected externally through connectors 82 of the manifold 8.

In a typical operation of the column, a packed bed of particulate stationary phase material fills the bed space 9 between the top and bottom filter layers 4. The valve devices 5 being closed, a mobile phase is fed in through mobile phase connector 81 (arrow "A"), passes through conduit 33 into the filtration space 34 and through the filter layer 4 to elute down through the packed bed, effecting separation of its components. Liquid eluate passes thought the filter layer 4 of the bottom end assembly 13 and out through the mobile phase connector 81 thereof (arrow "B") for collection as appropriate.

FIG. 1 and the above explanation are to illustrate general relationships of components and a typical mode of operation. The skilled person knows, and it will also appear from the following description, that other specific constructions and modes of operation may be appropriate for different kinds of process.

A more detailed embodiment of an end plate and valve construction is now described with reference to FIGS. 2 and 3.

A manifold 8 is provided as a machined metal or plastics block fixed sealingly over the central opening 31 of the end plate 3 by threaded connectors 88, and recessed into a central aperture 23 of an outer metal retaining plate 2 which is fixed to the end plate 3 by bolts 21 or other suitable fasteners. The periphery of the end plate 3 seals against the column side wall 11 with an annular polymeric seal member 32 which also overlaps the filter layer 4 to retain its periphery. This seal member may have an internal rigid reinforcement. Unlike a conventional O-ring it eliminates dead space by sealing with a cylindrical surface and mounting in a shape-fitting groove of the end plate.

The manifold 8 has a central bore 91 coaxial with the plate opening 31 and having inwardly and outwardly directed threaded connection openings 83, 89. The cylindrical barrel 6 of a spool valve 5 is screwed into the inward connection 83, to extend coaxially inwardly through the central plate opening 31 and out through a central circular orifice 41 of the filter layer 4, terminating in an outward flange 65 which overlaps the filter layer 4. A cylindrical outer sleeve 66 fits snugly around the barrel 6, its outward edge resting against the inward face of the manifold block through a polymeric sealing ring 662 and its inner edge resting against the outer surface of the filter layer 4 through another polymeric sealing ring 661, trapping the layer 4 between the sleeve 66 and barrel flange 65. Since the barrel's outer diameter corresponds to that of the layer orifice 41, it is possible in the illustrated condition to remove the barrel by unscrewing it and withdrawing it inwardly, without disturbing the filter layer 4. This is an advantage for column maintenance.

One or more flow conduits 33 are created by clearance between the barrel assembly (barrel and sleeve) and the plate opening 31. Thus, the plate opening 31 may have a plurality of axially-extending channels distributed around it to form the conduits 33, intervening surfaces of the opening 31 fitting against the barrel assembly. Or, a full annular clearance may be provided. Or, these conduits may be provided away from the barrel assembly, defined only through the material of the plate 3. The inner ends of the conduits 33 communicate into the filtration space 34. Their outer ends align sealingly (by virtue of polymeric sealing rings 662, 663) with connection conduits 811 of the manifold block, connected in common to a threaded or otherwise connectable port 81. This establishes direct fluid communication between filtration space 34 and the port 81, while communication between the bed space 9 and port 81 is necessarily through the filter layer 4. Ribs provided on the inner plate surface 35 (in known manner) assist even distribution or collection of fluid to or from the space 34.

A bore 61 extends axially through the barrel 6 from one end to the other. The bore's outward end merges sealingly (by polymeric sealing ring 664) and without change of diameter into the central manifold bore 91. The inward end of the bore 6 is on the bed space side of the filter layer 4, and constitutes a mouth opening 611. The bore 61 has a uniform cylindrical cross-section except for a radially-enlarged portion near but outward of the mouth 611. The enlarged portion 612 has a central cylindrical part bordered on either side by tapering surfaces 613. These are angled at not more than 450 from axial.

A central probe element 7 acts in the bore 61, to give the function of a spool valve. The probe element 7 has an elongate tube 72 with an open internal bore 73, extending axially from adjacent the barrel mouth 611 out through the outward end of the barrel 6 and the coaxial ball 91 of the manifold 8. Outwardly of the outer barrel end, a tapered sealing ring 665 seals between the tube 72 and surrounding manifold ball 91: a plug collar 87 is screwed into the outer connection 89 of the manifold to hold the tapered seal 665 effectively in place.

At its inward end, the probe 7 has a solid head 71 with a pointed tip 74, terminating the bore 73. The head 71 has a cylindrical sealing surface 711, of the same diameter as the barrel bore 61, and which as shown can seal against an inward sealing surface 64 at the mouth 611 of the barrel bore 61, assisted by a flush-recessed polymeric sealing ring 641.

The probe bore 73 opens at a set (FIG. 4) of spray openings 75 opening through and distributed circumferentially around the tube 72. The tip sealing surface 711 stands radially proud of these openings 75. Immediately outwardly of the openings the probe head 71 has another radially-enlarged portion or land 76 which presents a cylindrical sealing surface 761 bordered by tapering portions 762 angled at not more than 45° from the axial.

Outwardly of this second enlargement 76 the tube exterior 72 is a plain cylinder.

The diameter of the sealing surface 761 on the second enlargement 76 is the same as that 711 on the first enlargement 71.

The tube 72 being narrower than the barrel ball 61, an annular-section clearance 51 is defined between them. This constitutes an outer valve conduit extending out through the outer end of the barrel 6 into the manifold bore 91 up to the seal 665, where it diverts to a threaded or otherwise connectable manifold port 82.

Beyond the manifold 8, the outer end of the probe tube 72 is connected to means for advancing or retracting it axially relative to the barrel 6, with sliding through the seal 665. These means may be motor or servo activated, e.g. advancing the probe 7 by rotating a fixed drive member which engages the tube 72 via a screw thread, e.g. as proposed in GB-A-2258415. Additionally or alternatively, a manual control is provided for the axial adjustment.

The spool valve effect of the valve 5 is as follows.

Figure 2:
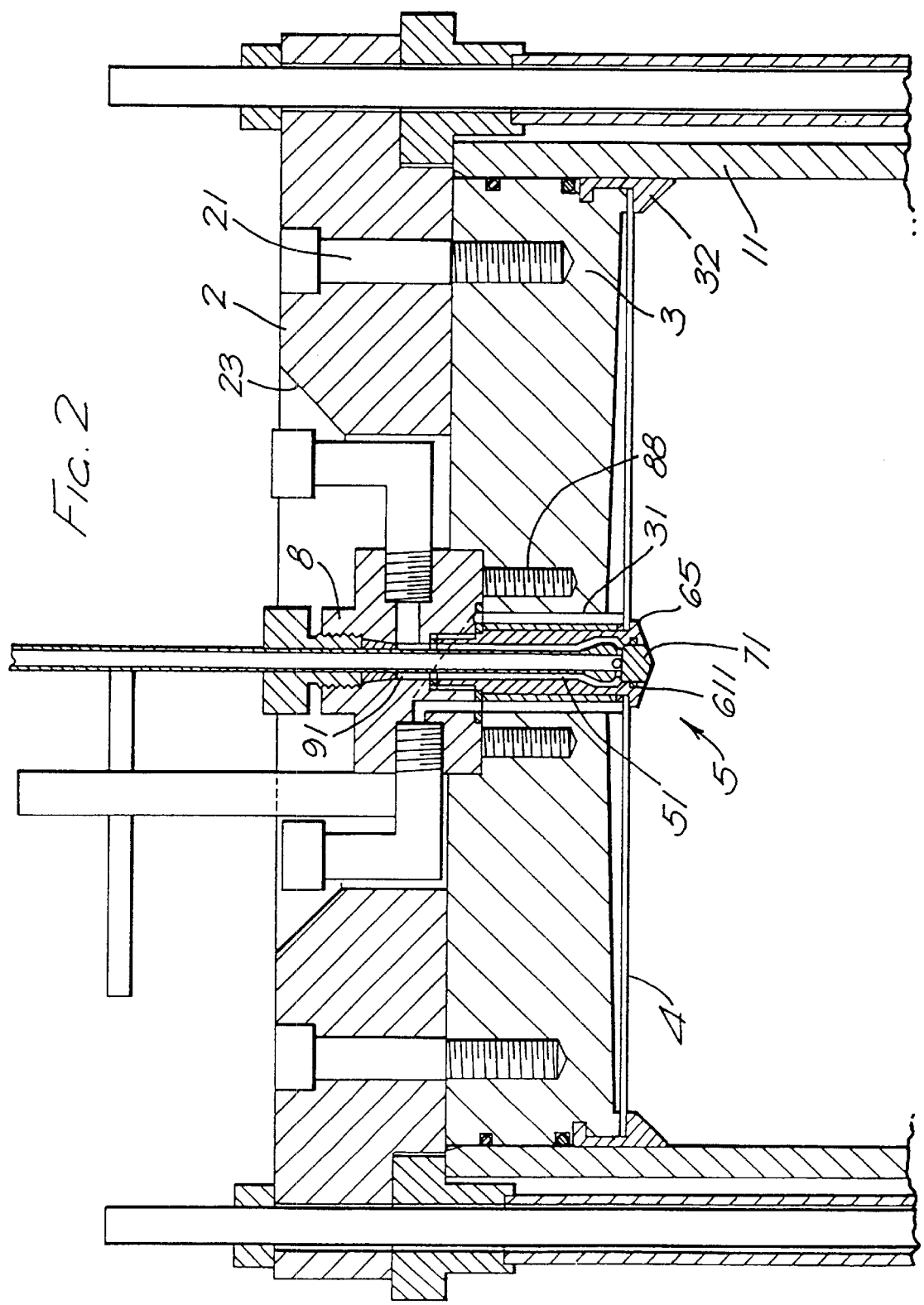
FIG. 2 is an axial cross-section showing an end plate construction in more detail.
Figure 3:
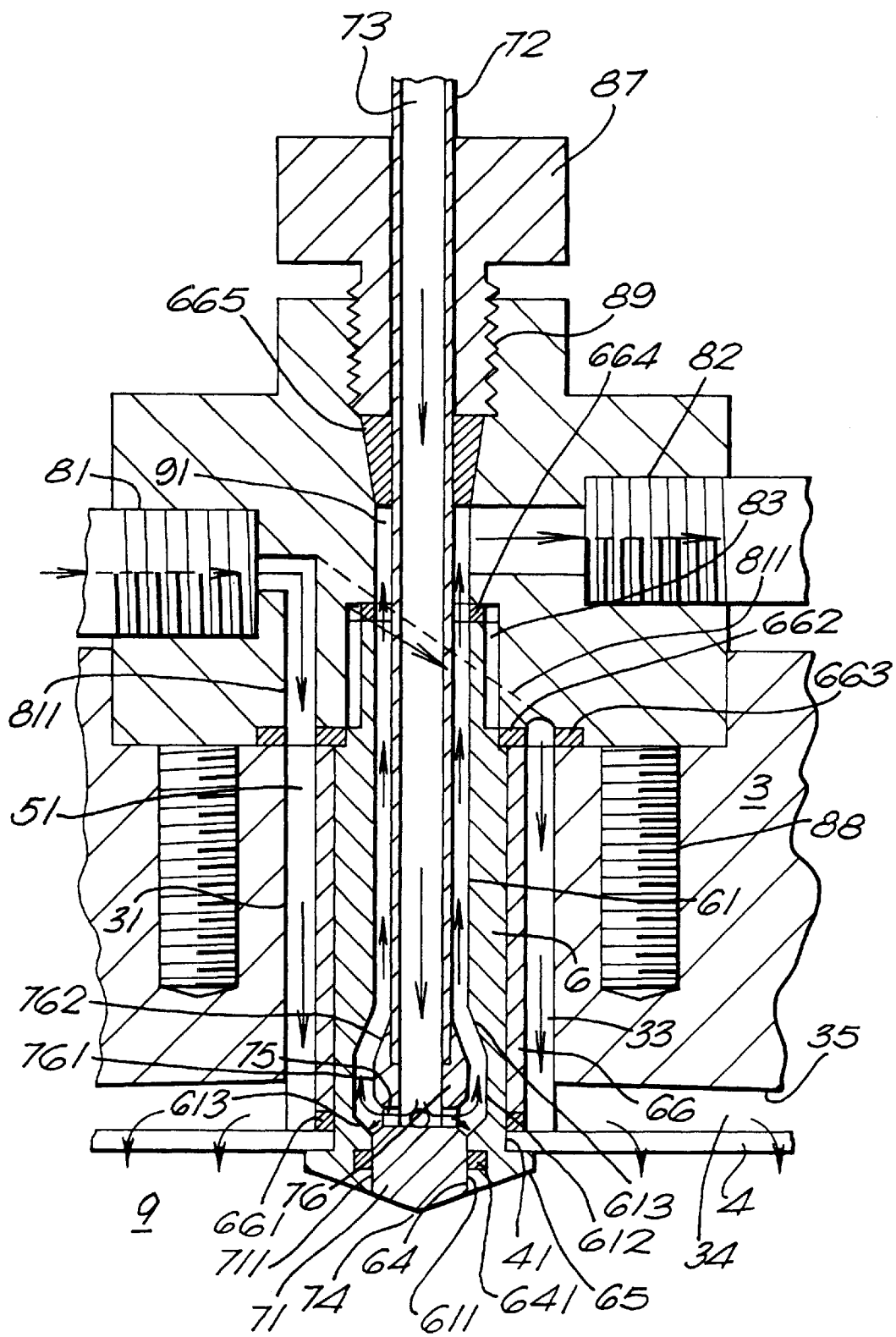
FIG. 3 shows enlarged, in axial cross-section, the construction of an access valve.

FIGS. 2 and 3 show a first, closed condition in which the head sealing land 711 seals with the mouth sealing surface 64 of the barrel, isolating both the valve conduits 51, 73 from the bed space 9. The filtration conduits 33 are not affected by the valve. The nozzle openings 75 and the second sealing land 76 register axially with the radially-enlarged portion 612 of the barrel bore 61. This puts the nozzle openings 75 into communication with the outer valve conduit 51, creating a continuous sealingly-enclosed flow path between the probe tube bore 73 and the manifold port 82. This path has no unswept areas or dead spaces. Within the valve device 5, none of its boundary surfaces deviates from the local central flow axis/layer by more than 45°, assisting effective sweeping. In the manifold the path likewise has no dead ends.

Consequently, when the chromatography column is running (see also FIG. 7) the valve device and its associated connections can be cleaned in place by feeding a cleaning solution (e.g. aqueous alkali, or other suitable cleaning medium known to the art) through that fully-sweepable cleaning path. It is particularly envisaged to feed the cleaning solution in through the probe tube 72.

FIG. 4 illustrates a second, partially-open condition of the valve 5. The probe tube 72 is advanced sufficiently to bring the second sealing land 76 into register with the bore mouth 611, where their respective sealing surfaces 761, 64 effect a sliding seal. This also brings the nozzle openings 75 to outside the mouth 611, communicating with the bed space 9. Accordingly the inner valve conduit constituted by the bore 73 is put into direct communication with the bed space, bypassing the filter layer 4, while the outer valve conduit 51 remains isolated from the bed space 9.

FIG. 6 illustrates an application of this in creating a new bed of packing material. The packing itself can be as described in GB-A-2258415. Specifically a flowable flurry of packing material particles in carrier liquid is pumped in through the tube 72 and sprays out radially in circumferentially-distributed directions from the openings 75. As packing material accumulates in the bed space 9 excess carrier fluid escapes through the filter layer 4 and away through the filtration conduits 33 and manifold port 81, to which a connecting tube is fastened. This is continued until sufficient packing material has been introduced.

FIG. 5 illustrates a third condition of the valve. Here the probe tube 72 has been advanced further inwardly to bring the second sealing land 76 clear of the mouth seal 64, which now opposes the smaller-diameter outer surface of the tube 72 to create a clearance, opening the outer valve conduit 51 to the bed space 9 through the mouth 611.

FIG. 8 shows how to exploit this third condition to unpack material from a column bed. It should be noted that, as disclosed in GB-A-2258415, the advanced pointed head 71 of the probe 7 is apt to disrupt existing bed material, which is often a hard compacted mass, and thereby help to initiate unpacking. A carrier liquid such as a buffer is pumped in through the probe bore 73 and out through the nozzle openings 75; its high nozzle velocity helps to disrupt and entrain the packed material. The particulate packing material cannot pass the filter layer 4, but it can respond to the pumping in of liquid by escaping as a slurry through the mouth 611 of the valve and along the outer valve conduit 51 to the manifold port 82 for discharge along a connected tube.

So, for the first time a single column wall installation enables both packing and unpacking of a column. This can give much greater flexibility in column operation. Note that the packing and unpacking operations can be effected entirely from outside the column housing, without needing to dismantle or remove the end assemblies. Furthermore the valve which can do this can itself be cleaned in place, even when the column is running by introducing a mobile phase onto the bed through the filtration conduits 33 as shown in FIG. 7. So, even this relatively sophisticated wall installation does not introduce a risk of contaminants accumulating and leaching into a long-running process perhaps with disastrous results. In the terminology of the skilled person in this field, this valve device is a "sanitary" installation.

Furthermore the valve is easily dismantled for maintenance because the probe 7 can be entirely withdrawn inwardly from the barrel bore 61.

Further modes of use, in relation to expanded-bed separation processes, are explained with reference to FIGS. 9 and 10. Expanded bed adsorption is a recently-developed separation technique, particularly for reducing or eliminating the need to clarify biological cultures before eluting them through a packing to separate out a desired component. The packing bed is expanded by an upflow of liquid medium so that even particulate material in the sample can work its way through the bed to the outlet above the bed. For expansion the bed must rest on a permeable layer through which the liquid up-flow is established. Introduction of the sample must therefore generally be done as a single pass, which sample batch then elutes through the bed. Usually desired materials are adsorbed onto the bed particles, and in a subsequent step are recovered by stopping the liquid up-flow, compressing the bed by moving down the upper plate and then percolating through the bed a liquid that desorbs the target substance from the bed particles.

A column for this can have top and bottom retaining assemblies which each have an impermeable plate interior filter layer and a central valve device as shown in the previous Figures. The normal filtration conduits and means for establishing up-flow of a mobile phase are also provided.

A first feature here is that a sample e.g. unclarified broth, can conveniently be introduced into the expanded bed, bypassing the lower filter mesh, by injecting it though the inner valve conduit 73 of the lower valve in its second, partially open condition. Where sample is injected intermittently the lower valve is returned to its fully-closed first condition in between. Our new valve construction therefore provides a convenient way of introducing such a sample past a mesh required for maintaining an up-flow.

A second and very significant feature is explained in relation to FIG. 9, which shows in more detail a top end assembly for the expanded-bed process.

During normal running of the process the mobile phase passes through the filter layer 4', through the filtration conduits 33' and out. There is a gradual accumulation of particulate debris and other matter reluctant to pass the filter 4, e.g. lipids. This therefore accumulates in an upper bed space region 91 adjacent to filter layer 4. In time it hinders the maintenance of proper flow.

By moving the upper valve device 5' to its third, fully-open condition for a short period of time, while creating a clearing flow of liquid adjacent the filter layer 4' to disturb the accumulated matter, this matter can be caused to follow the clearing flow out of the bed space via the outer valve conduit 51. One method of achieving a clearing flow is to provide a short blast of suitable liquid, e.g. a buffer, through the probe bore 73' and out through the nozzle openings 75' which are near the filter layer 4'. Alternatively or additionally, the normal flow direction (arrow "X") of buffer out of the system can temporarily be reversed and buffer pumped back in through the filtration conduits 33' (arrow "Y"), thereby creating a temporarily downward flow through the filter layer 41 (arrow "Z"), disrupting the accumulated material so that it can accompany the escape of the temporary liquid pressure wave out through the valve conduit 51. This may be done either with or without cutoff of the supply of sample at the bottom of the column.

Thus, the process can be run as long as the absorption proceeds efficiently, without needing to stop for other reasons. This is a highly advantageous procedure.

FIG. 10 shows a variant end plate construction for a chromatography column. The differences from the previous embodiment include the following.

The filter layer 4 is formed integrally with inner and outer annuli 41,42, in one piece in plastics material.

The inner annulus 41 forms a flush termination for the barrel 6 of the central valve 5, and has an inwardly-facing surface to form the seal with the valve's central probe. This flush one-piece construction further reduces the risk of contamination at the point of access. It also enables the filter layer's inner periphery to self-trap in a groove of the valve barrel 6, enabling that barrel 6 to be one component rather than two. The end cell and valve components may be of polypropylene.

The filter layer's outer annulus 42 is used to hold the filter layer in place by trapping between the wall 11 of the column and the end plate 3 of the cell, which in this version is a one-piece polypropylene construction.

The connection manifold 8 has the mobile phase inlet/outlet port 81 and the waste slurry outlet port 82 inclined outwardly, rather than perpendicularly as in the previous embodiment, to improve flow. A further significant feature in this embodiment is that the filter layer 4 is concave, by virtue of the support ribs on the end plate 3 being formed with inclined rather than slightly radial edges. We find that this slight conicity improves drainage from the column during clearing.

FIG. 11 shows schematically a different embodiment valve which however embodies similar concepts. Here the central movable probe is a simple armature rather than a fluid-carrying nozzle. Its enlarged head 171 is carried on actuating rod 272 and has a flat end surface 1712, a first outer sealing land 1711, a conical convergence 1613 to a narrow recess or waist 1612, and a smaller enlargement 176 with a second sealing surface 1761.

The mobile phase conduit 33 is provide outside the valve barrel 6 as before. Inside the valve barrel the central fluid conduit 173 is defined not through the probe 272,171 but rather by an inner conduit wall 172 surrounding the probe shaft 272 and having an opening with an inwardly-directed seal 174, recessed back from the main opening through the filter layer 4, which has its own inwardly-directed seal 141 at the mouth of the outer conduit defined between the outer barrel wall 6 and the inner conduit wall 172.

FIG. 11 shows the valve fully open, with the central probe fully advanced to open both conduits e.g for unpacking and column. Unpacking liquid is pumped in through the inner conduit 173 and squirts out around the armature head 171; waste slurry flows back and out through the outer conduit.

In the partially open position, e.g for packing a column, the armature is partially retracted so that second sealing surface 1761 seals off the inner conduit, the outer conduit remaining open. Slurry can be pumped in through the outer conduit. This shears the slurry less than the spray nozzle of the first embodiment.

Full retraction of the armature brings its front surface 1712 flush with the filter layer 4 and its first head sealing surface 1711 into sealing engagement with the central filter opening seal 141, closing off the outer conduit. At the same time the second sealing land 176 drops below the inner conduit seal 174 which then opposes the recess 1612 to permit a circulating, clean-in-place flow through the inner and outer conduits.

Note that in the open conditions the conical portion 1613 of the head 171 can be axially adjusted to alter the direction of liquid pumped in. This embodiment illustrates how two separate seals on the fixed part of the valve can provide the same effect as previously if their spacing is different from that of the corresponding sealing portions of the movable part.

What is claimed is:

1. A separation process for separating a target component from a liquid incorporating the target component with one or more other components, the separation process comprising
    providing a bed of particulate packing medium, said medium being adapted to retain the target component and said bed thereof being enclosed in a bed space defined by a column housing, said housing having a process outlet and a restricted permeability element between the process outlet and bed space to retain the particulate packing medium in the bed space;
    flowing liquid upwardly through the bed of particulate packing medium, through the restricted-permeability element and through the process outlet, to expand the bed in the bed space and effect separation of the target component from the liquid through retention by the particulate packing medium;
    said one or more other components of the liquid comprising particulate matter, said particulate matter accumulating against the restricted-permeability element during the flowing of the liquid, and the process further comprising
    opening a clearing outlet communicating directly with the bed space, at or adjacent the restricted-permeability element, and
    forcing a clearing flow of fluid relative to the restricted permeability element to disturb the particulate matter which has accumulated against it, and causing said matter to pass out of the bed space through the clearing outlet.

2. A separation process as claimed in claim 1, in which the liquid comprises unclarified or partially-clarified cell culture broth, and the target component is a protein product in the culture broth.

3. A separation process as claimed in claim 1 in which the clearing flow comprises a reverse flow forced back through the restricted permeability element.

4. A separation process as claimed in claim 3, wherein said reverse flow travels through said process outlet and communicates directly with the bed space by passing through said restricted permeability element.

5. A separation process as claimed in claim 1 in which a said clearing flow is forced through at least one nozzle at the bed space side of the restricted-permeability element.

6. A separation process as claimed in claim 5 in which a said nozzle is on a conduit at the centre of the restricted-permeability outlet, and the clearing flow radiates from the nozzle.

7. A separation process as claimed in claim 5 wherein the clearing flow includes passing flow through said at least one nozzle and also through a channel defined by s aid process outlet.

8. A separation process according to claim 1 comprising flowing liquid upwardly through the bed of a particulate packing material concurrently with the flow of the clearing flow.

9. A separation process as claimed in claim 1 in which the column housing has a housing wall and an access valve is provided through the housing wall and restricted-permeability element to enable communication of first and second fluid flow conduits directly into the bed space, said access valve being adjustable between a closed condition in which said conduits are isolated from the bed space and an open condition in which said conduits are open to the bed space;

said access valve being adjusted in the process to the open position whereupon said second fluid flow conduit provides the clearing outlet and a said clearing flow of fluid is introduced through the first fluid flow conduit.

10. A separation process as claimed in claim 1 in which the column housing has an inlet-side restricted-permeability element and said flowing comprises pumping liquid medium through the inlet-side restricted-permeability element to expand the bed, and an inlet-side access valve movable between open and closed conditions is provided to communicate directly with the bed space, a material containing said target component being introduced directly into the bed space through said inlet-side access valve in its open condition.

11. A separation process as defined in claim 10 in which said material comprises an unclarified or partially-clarified culture broth, and the target component is a protein product in the culture broth.

12. A separation process as claimed in claim 10 in which the inlet-side access valve opens at the center of the inlet-side restricted permeability element.

* * * * *